Figure 1:
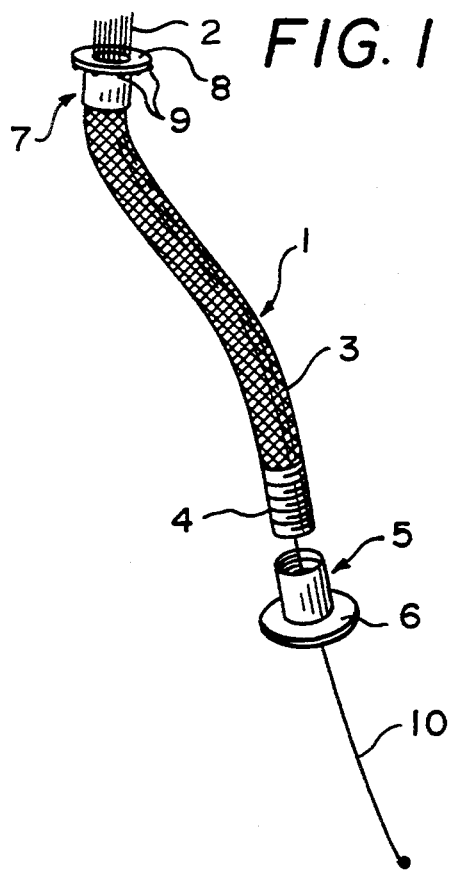

United States Patent [19]

Bowald

[11] Patent Number: 5,425,766
[45] Date of Patent: Jun. 20, 1995

[54] RESORBABLE PROSTHESIS

[75] Inventor: Staffan F. Bowald, Almunge, Sweden

[73] Assignee: Astra Tech Aktiebolag, Molndal, Sweden

[21] Appl. No.: 13,221

[22] Filed: Feb. 1, 1993

Related U.S. Application Data

[63] Continuation of Ser. No. 570,547, Aug. 21, 1990, abandoned, which is a continuation of Ser. No. 399,498, Sep. 11, 1989, abandoned.

[30] Foreign Application Priority Data

Mar. 9, 1987 [SE] Sweden ................................. 8700969

[51] Int. Cl.$^6$ ................................................. A61F 2/08
[52] U.S. Cl. ................................................. 623/13
[58] Field of Search ....................... 623/1, 2, 13, 16, 18, 623/66

[56] References Cited

U.S. PATENT DOCUMENTS

| | | | |
|---|---|---|---|
| 3,982,543 | 9/1976 | Schmitt et al. | 623/13 |
| 4,127,902 | 12/1978 | Homsy | 623/13 |
| 4,467,478 | 8/1984 | Jurgutis | 623/13 |
| 4,713,075 | 12/1987 | Kurland | 623/13 |
| 4,923,470 | 5/1990 | Dumincan | 623/13 |
| 4,942,875 | 7/1990 | Hlavacek et al. | 623/13 |
| 4,946,377 | 8/1990 | Kovach | 623/13 |

FOREIGN PATENT DOCUMENTS 8806872  9/1988  WIPO ................................. 623/13

*Primary Examiner*—David Isabella
*Attorney, Agent, or Firm*—Bacon & Thomas

[57] ABSTRACT

An implantable prosthesis for completely or partially replacing a tendon, a ligament or a cruciate ligament is characterized by a structure of bioresorbable material other than proteins, polypeptides and derivatives thereof, which structure exhibits longitudinal grooves or channels intended to server as initial propagation guides for new fibrous tissue.

13 Claims, 1 Drawing Sheet

RESORBABLE PROSTHESIS

This application is a continuation of application Ser. No. 07/570,547, filed Aug. 21, 1990, now abandoned, which is a continuation of 07/399,498, filed Sep. 11, 1989, now abandoned.

The present invention relates to an implantable prosthetic element for the reconstruction of tendons, ligaments and cruciate ligaments of a human or an animal.

Injuries to tendons, ligaments and cruciate ligaments are very frequent and principally happen to younger persons, often in connection with the exercise of athletics or sports.

The conventional way of repairing torn off tendons, ligaments and cruciate ligaments (ligaments in the knee joint) has been to fasten the tendon or ligament ends together by means of a suture. In the case of more extensive injuries, such that loss of substance must be bridged, one has been reduced to various types of tendon plastic.

The possibilities of repairing tendons, ligaments and cruciate ligaments with a satisfactory result by this conventional method have been very restricted. This fact may partially be attributed to the very special structure of the tendon tissue to withstand load only in one direction (characteristic fibre structure poor in cells and vessels and with substantially longitudinal collagen fibres as the supporting part). In addition to the healing rate after an injury being very low, severed or torn off tendons or ligaments repaired in this conventional way propagate with unorganized connective tissue which will obtain a lower strength than that of the original tissue. Further, this scar tissue often spreads into surrounding structures, which will have a restrictive influence on its mobility.

To this should be added the effects of the fact that the body part in question due to the poor healing rate must be kept immobilized for a very long time, usually from six weeks up to six months, which results in stiffness of the unloaded joints, decalcification of the skeleton and muscle atrophy.

In recent years prostheses of materials without adverse tissue reaction, such as Dacron, Teflon and polypropene, have been used to a certain extent for repairing tendons, ligaments and cruciate ligaments. While it has been possible hereby to reduce the time that the patient must keep the body part in question immobilized, and thereby to avoid some of the above mentioned disadvantages, these prostheses have usually resulted in the formation of granuloma and incomplete function. In particular for cruciate ligament prostheses it has not been possible to obtain either a satisfactory stability of the knee joint or the necessary strength of the tissue formed upon healing, and after long time use the prostheses have been found to break due to fatigue of the material.

It has also been proposed to combine permanent prostheses of the type described above with a material resorbable in the body to promote and improve the ingrowth of new tendon and ligament tissue, respectively. For example, the U.S. Pat. Nos. 4,127,902 and 3,971,670 describe structures consisting of a combination of a load absorbing component of a biocompatible, but non-resorbable material and a component of a resorbable porous material intended to promote the ingrowth of life tissue.

The U.S. Pat. No. 3,463,158 discloses the use of composites of polyglycolic acid and non-absorbable fibre materials as implantates for the repair or replacement of tissue, the composites being designed such that the new tissue will surround the non-absorbable fibre material.

However, no completely successful results with these types of prostheses have been reported so far.

Also carbon fibre structures have been tested as a replacement for injured tendon or ligament tissue. It has, however, been found that the carbon fibre structure is degraded mechanically in the course of time and that the carbon fibre fragments then tend to migrate into the body from the site of the surgery. To obviate this problem the U.S. Pat. No. 4,411,027 suggests covering the carbon fibre structure with a layer of a bioabsorbable polymer in order to, on one hand, keep the fragments in position at least during the early healing stage. It has, however, been found that carbon fibre fragments from the prosthesis still migrate into the body.

The U.S. Pat. Nos. 3,397,033; 3,636,595 and 3,982,543 only quite generally propose the use of tubular structures of bioabsorbable polymers in the form of polyglycolic acid, lactide polymers and copolymers of lactic acid and glycolic acid, respectively, for the repair of various body parts, including tendons, without describing the proposed applications in any detail.

WO 85/0511 discloses a ligament or tendon replacement of natural collagen treated with glutaraldehyde, the collagen being provided in the form of a weave with sufficient space between the strands thereof to permit the propagation of fibroblasts therethrough for regeneration of the tendon or ligament. In one embodiment a sheet of the weave has been rolled into a coil to form a three-dimensional network structure. However, collagen has proved to be an unsuitable material in these connections. Even if the treatment with glutaraldehyde reduces the antigenicity, a foreign body reaction is obtained, giving rise to scar tissue with reduced function of the regenerated tendon or ligament.

The object of the present invention is to provide an improved prosthetic element which completely or partially may replace a tendon, a ligament or a cruciate ligament and which has not the above mentioned disadvantages of the hitherto known prostheses. The novel prosthetic element should thus stabilize the tendon, ligament or cruciate ligament during the whole healing process. Further, the structure of the prosthetic element should be such that it controls the reconstruction of collagen in the new tissue to resemble as much as possible the original tissue that it is to replace and have essentially the corresponding function. Concerning ligaments and cruciate ligaments also bone should be capable of growing into the new structure. Finally, the prosthetic material as a whole should be capable of disappearing from the body without leaving any residues. These objects, as well as other objects and advantages, are obtained with a prosthetic device having the features stated in the accompanying claims and which are further explained below.

According to a basic concept of the invention the prosthetic element completely consists of a substantially water-insoluble, non-toxic bioresorbable material without adverse tissue reaction, with the exception of proteins, polypeptides and derivatives thereof, which bioresorbable material can be degraded and resorbed completely in the body without giving rise to scar tissue or toxic degradation products, and additionally has a special structure which, on one hand, should be capable of providing the necessary strength (particularly important for cruciate ligaments) and, on the other hand, be capable of promoting and controlling the ingrowth of new tissue in a suitable direction.

In the broadest aspect thereof this structure is characterized in that it exhibits longitudinal grooves or channels intended to serve as initial propagation guides for new fibrous tissue. The terms grooves and channels, respectively, are herein to be understood in a broad sense, and to comply with the objects of the invention the structure may be arranged in a great number of different ways as will appear from the following.

Thus, in one embodiment it may simply consist of a single, or possibly more, elongate element(s), each of which is provided with several longitudinal grooves or channels. These grooves or channels may be provided on the outside of the element or extend within .the element, possibly in combination. As an example, in the former case the prosthetic element may be provided with the necessary grooves already in the manufacture thereof, e.g. by extrusion, but it may also consist of an initially sheet-shaped piece of material which has been folded to a suitable configuration. An example of such a prosthetic element having inner channels or cavities is a sheet that has been rolled to obtain a helical cross-section.

According to another embodiment the prosthetic element structure according to the invention is built-up from a plurality of elongate members, which define longitudinal channels or cavities between them. Preferably, these elongate members are arranged to be substantially individually load absorbing when the prosthesis is applied. For example, they may consist of threads or fibres, in which case the assembly thereof may be straight, or braided, twined or rotated. They may also consist of a plurality of parallel laminar, leaf- or strip-shaped members. Another alternative is a plurality of concentrically disposed cylinders or tubes. The individual members may in these cases be whole, optionally perforated material pieces, but may, e.g., also consist of net or be knitted, woven or braided structures, etc. Also a folded structure may be comprised by .this embodiment, in the case of, e.g., a weave the load absorbing members corresponding to the warp-threads. The cavities of a perforated, net-shaped or knitted structure must, of course, not be so large that the propagation guiding function of the longitudinal grooves or channels is influenced to any considerable extent.

As mentioned above the design and dimensions of said grooves or channels of the prosthetic element structure may vary considerably, but for the desired penetration of cells into, e.g. inner channels or cavities to take place, the latter should have a minimum cross-sectional dimension of about 10 $\mu$m.

The resorption period of the prosthetic element structure according to the invention should be sufficiently long for the structure to be a stabilizing replacement until the new tissue has been sufficiently regenerated to absorb loads itself. This period will, of course, depend on the type and the extension of tissue to be replaced but may generally be said to be about six months to about two years.

In the same way the strength requirements vary according to the tissue to be replaced, and therefore the strength requirements are relatively high in case of a cruciate ligament, while they, of course, may be relatively low for, for example, a finger tendon.

As to the cross-sectional dimensions of the actual prosthetic element may, as examples, be mentioned about 1 to 2 mm for minor tendons up to two centimeters (the Achilles tendon), and, e.g., for cruciate tendons about 4–5 millimeters.

In use the prosthetic elements according to the invention will function as a load absorbing replacement for the tendon, ligament or cruciate ligament that they are to replace, such that loading of the body part in question may take place almost immediately after the surgical operation. Such immediate loading has proved to accelerate the healing process and favourably influence the cell differentiation. Concurrently with the growth of the new tissue the prosthetic material is slowly degraded and resorbed in the body, the new tissue successively taking over the load absorption. In connection therewith the special structure according to the invention has proved to function as an efficient scaffold for the new tissue while successively guiding the same along the elongate elements, such that the eventually formed new tissue at least to a very large extent will resemble the original tissue.

In an advantageous form of the prosthetic structure the different individual members have two or more different resorption periods, which, for example, easily may be achieved by varying the thickness of the members and/or by the choice of material.

The individual members of the prosthetic structure may consist of a single material, but to obtain the desired resorbability and strength of the prosthesis as a whole it may be necessary to utilize a combination of different materials. For example, each individual member may have a core of a material with high strength, but which is relatively quickly resorbable and an outer covering of a material with low strength but with a longer resorption period.

According to one embodiment of the invention the prosthetic element structure is surrounded by a porous outer covering of bioresorbable material, for one thing, when necessary, for the purpose of holding the inner structure together, but above all to reduce the entry of body fluids to the inner structure and thereby to adequately delay the chemical attack thereon to prolong the resorption period, which may be of importance depending on the resorbable material chosen. Further, the outer covering will advantageously serve as a scaffold for blood vessels and fibroblasts penetrating from the outside.

The porosity of the outer layer should, however, be sufficient to permit the penetration of blood cells and fluids and is suitably such that at least half of the pores are in the range of between about 10 and about 200 $\mu$m, the pores preferably, however, not being larger than 150 $\mu$m.

The outer layer, which substantially is not load absorbing, may consist of a separate cover structure, e.g., net-shaped, but it may also be a layer that has been deposited or coated on the inner structure in any suitable manner.

As a suitable resorption period of the outer layer may be mentioned about 3 to about 12 weeks, which depending on the material choice usually will give a layer of the order of 0.1–0.5 mm.

The outer shape of the prosthetic element is not critical per se and is adapted to the structure to be replaced.

Suitable bioresorbable materials for the purposes of the present invention and corresponding to the above given definition may readily be selected by the person skilled in the art, e.g., among those materials which are either commercially available or have been described in the literature or will be available in the future. Particularly useful are aliphatic polyesters. As examples of specific bioresorbable materials may be mentioned polymers based upon polyglycolic acid (PGA), copolymers of glycolic acid and lactic acid, copolymers of lactic acid and ε-aminocaproic acid, and various lactide polymers. PGA esters are, e.g., described in the U.S. Pat. No. 3,463,658, while copolymers of glycolic add and lactic acid are described, e.g., in the U.S. Pat. No. 3,982,543. Homo- and copolymers of lactic acid are described, e.g., in the U.S. Pat. No. 3,636,956. Examples of now commercially available materials are Vicryl ® (a copolymer of 90% glycolic add and 10% lactic add marketed by Ethicon, Sommerville, N.Y., U.S.A.—also known as Polyglactin) and Dexon ® (Davies & Geck, Pearl River, N.Y., U.S.A.). Further examples are polydesoxazon (PDS) (Ethicon, U.S.A.), polyhydroxybutyric acid (PHB), copolymers of hydroxybutyric acid and hydroxyvaleric acid (PHB-PHV), polyesters of succinic acid, and crosslinked hyaluronic add. As mentioned above, of course, also mixtures of the above materials may be used. The person skilled in the art would easily be able to modify such bioresorbable materials according to the needs in each specific case, e.g., concerning porosity, resorption period, strength, etc.

Optionally, growth factors may be incorporated in the prosthetic structure, either deposited in the mentioned cavities or incorporated into the resorbable material for slow release of growth factor.

Figure 2:
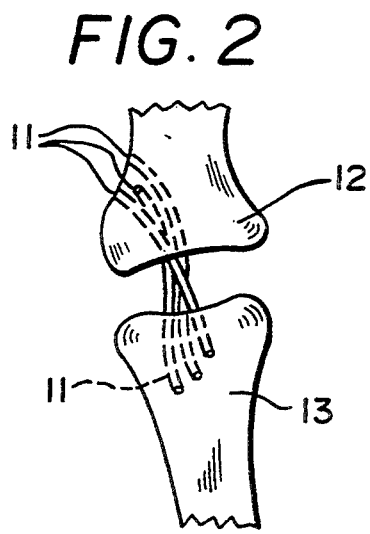
Figure 11:
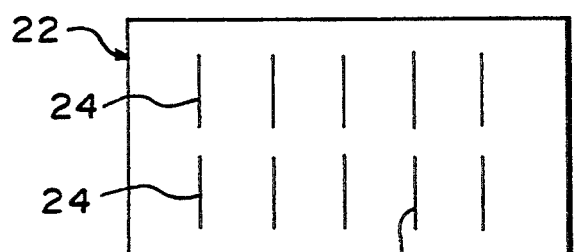
Figure 9:
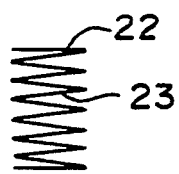
Figure 10:
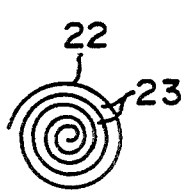

Hereinafter the invention will be described in more detail with regard to a particular embodiment of the invention for replacement of a cruciate ligament, reference being made to the accompanying drawings, in which:

FIG. 1 is a schematic perspective view of an embodiment of a prosthetic element according to the invention, FIG. 2 schematically illustrates the application, as a cruciate ligament replacement, of three prosthetic elements according to FIG. 1 in a knee joint, FIGS. 3 to 10 show schematic cross-sections of alternative embodiments of the prosthetic element according to the invention, and FIG. 11 schematically illustrates a piece of a helical structure according to FIG. 10 before coiling.

The prosthetic element of FIG. 1, which is generally designated by the reference numeral 1, comprises an inner structure in the form of a plurality of threads 2 of a suitable bioresorbable material or material combination, which have been twined to form a multi-filament strand of a desired thickness and been provided with an, in the illustrated case, net-shaped outer covering or coating 3 of a suitable bioresorbable material.

As an example, the threads 2 may be composites consisting of a core of Vicryl ® and an outer layer of PHB, which have been bundled and twined and then been provided with a coating of PHB and PHV. The coating may, e.g., be applied by dipping the twined filament bundle first into a solution of PHB and PHV in dimethylacetamide (DMA), and then into water. A suitable porous outer layer of PHB-PHV is then precipitated onto the twined structure.

The prosthetic element 1 is, in the illustrated case, intended to be used as a cruciate ligament replacement, in which case three such elements are used, but the structure as such may generally be used for all kinds of tendons and ligaments.

For the cruciate ligament application the threads 2 and the outer covering 3 are attached to an externally threaded end cap 4 at the lower end of the prosthetic element 1, to which end cap each thread 2 is individually fixed. An internally threaded lower fixing sleeve 5 with an end flange 6 is arranged to be screwn onto the end cap 4. An upper fixing sleeve 7 is slidably arranged on the prosthetic element 1 and has an end flange 8 provided with inwardly facing pointed projections or spikes 9. The end cap 4 as well as the fixing sleeves 5, 7 may consist of a bioresorbable material or of a suitable non-resorbable material without adverse tissue reaction, such as titanium. A guide wire 10 extends from the lower end of the prosthetic element 1.

FIG. 2 schematically illustrates the application of three prosthetic or cruciate ligament elements 1 in a knee joint which has been provided with suitably disposed bores 11 in the two joint portions 12, 13. The arrangement of cruciate ligament elements 1 shown in the figure is intended to be isometric, i.e. the cruciate ligament elements 1, on the basis of the known movement pattern the joint, having been placed with their fibre or thread directions such that loads are absorbed and the joint is stabilized in three different main directions during the joint movement.

When applying the cruciate ligament prosthesis of FIG. 2 each cruciate ligament 1 is introduced into its respective bore 11 by means of the guide wire 10. The length of the cruciate ligament is then adjusted with the upper fixing sleeve 7, which is fixed to the cruciate ligament, e.g., by damping, and simultaneously in the bore opening via the projections 9. The application is completed by screwing the lower fixing sleeve 5 onto the end cap 4 while simultaneously adjusting the tension of the cruciate ligament.

Practically immediately after the surgical operation the illustrated cruciate ligament prosthesis is ready to absorb loads. New ligament tissue will grow into the interspaces between the threads 2 and obtain an advantageous successive orientation in the longitudinal direction. Simultaneously the prosthetic material will slowly be subjected to hydrolysis and/or enzymatic degradation, which at least during the initial period of the healing process is suitably delayed by the outer structure 3, which additionally will serve as a scaffold for inter alia blood vessels. The possibility of loading the knee joint already from the beginning will contribute to an efficient regeneration of the ligament tissue owing to the fact that the natural movements promote the differentiation of the new cells. Concurrently with the prosthetic material being resorbed, a successive regeneration of the ligament tissue will take place to ultimately result in a collagen-rich tissue oriented in parallel bundles and very like a normal cruciate ligament.

Of the examples of different alternative embodiments of the prosthetic element according to the invention schematically illustrated in FIG. 3–11, FIGS. 3 and 4 relate to prosthetic elements which in conformity with that of FIG. 1 are built up from a plurality of subelements, while FIGS. 5 to 11 show prosthetic elements based upon one single element.

Figure 3:
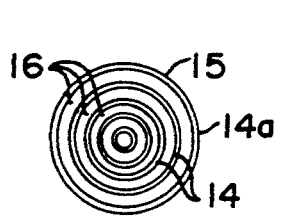

The prosthetic element structure of FIG. 3 consists of a schematically illustrated assembly of a plurality of concentrically arranged tubular or cylindrical members 14 of a bioresorbable material, the outermost tubular member 14a being surrounded by or coated with an outer covering or layer 15, also of a bioresorbable material. The members 14 define annular channels or cavities between them which in the figure are very exaggerated; in practice, however, the members 14 may contact each other and still leave the necessary interspaces.

Figure 4:
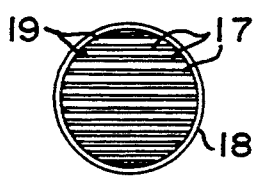
Figure 5:
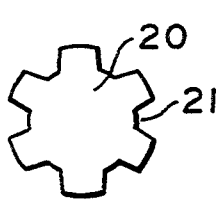
Figure 6:
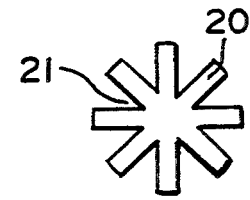
Figure 7:
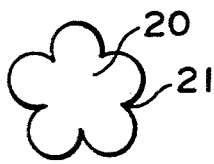
Figure 8:
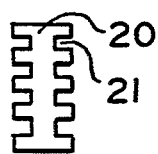

In the embodiment according to FIG. 4 the inner structure consists of a plurality of laminae or bands 17 of a bioresorbable material which are kept together by an outer covering or layer 18 of a bioresorbable material. The bands 17 define channel-shaped passages or cavities 19 between them which are very exaggerated in the figure. Also in this case the bands 17 may in practice contact each other.

The embodiments according to FIGS. 5-8 all consist of a solid elongate element 20 shaped into different configurations exhibiting external grooves or channels 21 which are to serve as propagation guides for the new tissue.

In the embodiments according to FIGS. 9 and 10, 11 the prosthetic element is formed from a film or foil 22, which in FIG. 9 has been folded and in FIGS. 10, 11 coiled. Propagation guiding grooves or channels 23 are in FIG. 9 formed by the folds, while in FIG. 10, 11 they are formed between adjacent coil layers. In FIG. 11 the film or foil 22 is provided with a plurality of longitudinal slits 24 to increase the penetration of cells and fluids from the sides thereof.

The prosthetic elements of FIGS. 5-11 may in conformity with the embodiments according to FIGS. 1-4) be provided with a covering or coating of a porous bioresorbable material (not shown).

Below an animal experiment is described wherein a cruciate ligament prosthesis according to FIGS. 1 and 2 was applied to sheep.

EXAMPLE

A cruciate ligament prosthesis according to FIG. 1 was made of bundles of PHB-PHV—coated Vicryl ® thread, which were twined to strands of about 3 mm thickness and were provided with a knitted hose of Vicryl ® to keep the strands together. In the individual threads the Vicryl ® material has a high strength with a relatively rapid resorption, which is balanced by the outer layer of PHB-PHV with a long resorption but a lower strength.

The anterior cruciate ligament was recessed on 10 adult sheep, anaesthetized with sodium pentothal, oxygen/laughing gas and Fluorbane. Two or three above described cruciate ligament prostheses were inserted either isometrically via bore channels or anti-isometrically. The latter attachment was made to determine the sensitivity to incorrect insertion. After reconstruction all knees were stable. Four months later half of the animals were killed and after another two months the rest of the animals were killed. A microscopic photo documentation was performed, whereupon the preparations were fixed in 4% formalin. The bone attachment was sawn out, whereupon the bone substance was decalcified and the cruciate ligaments were section-cut for macroscopic analysis. A regenerate was taken for strength test.

As a result all the cruciate ligaments showed good regeneration. There was no difference between isometrically implanted and anti-isometrically implanted cruciate ligament prostheses. On anti-isometric implantation, however, varying degrees of arthrosis were found.

The microscopic analysis showed excellent regeneration of collagen-rich tissue oriented in parallel bundles and very like the picture of a normal cruciate ligament.

The invention is, of course, not restricted to the embodiments particularly described above and shown in the drawings, but many variations and modifications are possible within the scope of the basic concept of the invention and the subsequent claims.

I claim:
1. An implantable prosthesis for completely or partially replacing a tendon, a ligament or a cruciate ligament; said prosthesis comprising:
   a core having upper and lower ends; said core being formed from one bioresorbable elongate element wherein said elongate element is shaped to form longitudinal propagation guides in the form of passages extending from said upper end to said lower end; said passages being defined by said elongate element;
   an outer covering disposed around said core whereby said outer covering extends from said upper end to said lower end and together with said core forms said prosthesis;
   said core and said outer covering being made from a water-insoluble, non-toxic, bioresorbable material selected from the group of polymers consisting of polyglyxolic acid, copolymers of glycolic acid and lactic acid, copolymers of lactic acid and aminocaproic acid, lactide polymers, homopolymers of lactic acid, polydesoxazon, polyhydroxybutyric acid, copolymers of hydroxybutyric and hydroxyvaleric acid, polyesters of succinic acid and cross-linked hyaluronic acid;
   the elongate element of the core including first and second portions wherein said first portion has one resorption period and said second portion has a resorption period which is different from said first period.
3. A prosthesis according to claims 1 or 2 wherein said outer covering is porous.
4. A prosthesis according to claims 2 wherein said elongate elements are filaments.
5. A prosthesis of claims 4 wherein the filaments are twined to form a strand.
6. A prosthesis according to claims 2 wherein said elongate elements are selected form the group consisting of substantially parallel laminae and concentrically arranged tubular elements.
7. A prosthesis according to claims 1 or 2 wherein said outer covering has a shorter resorption period than the core.
8. A prosthesis according to claims 1 or 2 which further comprises
   an externally threaded end cap attached to the lower end of the covered core;
   an internally threaded lower fixing sleeve having an end flange thereon; said thread fixing sleeve being adapted to thread onto said threaded end cap;
   an upper fixing sleeve slidably arranged on said covered core; said fixing sleeve having an end flange thereon and said end flange being provided with inwardly facing pointed projections; and
   a guide wire extending from said lower end of the coated core.
2. An implantable prosthesis for completely or partially replacing a tendon, a ligament or a cruciate ligament; said prosthesis comprising:
   a core having upper and lower ends; said core being formed from a plurality of bioresorbable elongate elements wherein said elongate elements are arranged to form longitudinal propagation guides in the form of passages extending from said upper end to said lower end; said passages being defined between said elongate elements;

an outer covering disposed around said core whereby said outer covering extends from said upper end to said lower end and together with said core forms said prosthesis;

said core and said outer covering being made from a water-insoluble, non-toxic, bioresorbable material selected from the group of polymers consisting polyglyxolic acid, copolymers of glycolic acid and lactic acid, copolymers of lactic acid and aminocaproic acid, lactide polymers, homopolymers of lactic acid, polydesoxazon, polyhydroxybutyric acid, copolymers of hydroxybutyric and hydroxyvaleric acid, polyesters of succinic acid and cross-linked hyaluronic acid;

said elongate elements of the core including first and second portions wherein said first portion has one resorption period and said second portion has a resorption period which is different from said first period.

9. The prosthesis of claims 1 or 2 wherein the core and outer covering have unequal resorption periods.

10. The prosthesis of claim 2 wherein the elongate elements are threads.

11. The prosthesis of claim 10 wherein the threads are twined to form a strand.

12. An implantable prosthesis for completely or partially replacing a tendon, a ligament or a cruciate ligament; said prosthesis comprising:

a core having upper and lower ends; said core being formed from one bioresorbable elongate element wherein said elongate element is shaped to form longitudinal propagation guides in the form of passages extending from said upper end to said lower end; said passages being defined by said elongate element;

an outer covering disposed around said core whereby said outer covering extends from said upper end to said lower end and together with said core forms said prosthesis;

said core and said outer covering being made from a water-insoluble, non-toxic, bioresorbable material selected from the group of polymers consisting of polyglyzolic acid, copolymers of glycolic acid and lactic acid, copolymers of lactic acid and aminocaproic acid, lactide polymers, homopolymers of lactic acid, polydesoxazon, polyhydroxybutyric acid, copolymers of hydroxybutyric and hydroxyvaleric acid, polyesters of succinic acid and cross-linked hyaluronic acid;

and said core and said outer covering having different resorption periods.

13. An implantable prosthesis completely or partially replacing a tendon, a ligament or a cruciate ligament; said prosthesis comprising:

a core having upper and lower ends; said core being formed from a plurality of bioresorbable elongate elements wherein said elongate elements are arranged to form longitudinal propagation guides in the form of passages extending form said upper end to said lower end; said passages being defined between said elongate elements;

an outer covering disposed around said core whereby said outer covering extends from said upper end to said lower end and together with said core forms said prosthesis;

said core and said outer covering being made from a water-insoluble, non-toxic, bioresorbable material selected from the group of polymers consisting of polyglyxolic acid, copolymers of glycolic acid and lactic acid, copolymers of lactic acid and aminocaproic acid, lactide polymers, homopolymers of lactic acid, polydesoxazon, polyhydroxybutyric acid, copolymers of hydroxybutyric and hydroxyvaleric acid, polyesters of succinic acid and cross-linked hyaluronic acid;

and said core and said outer covering having different resorption periods.

* * * * *